(12) United States Patent
Liu

(10) Patent No.: US 10,933,029 B2
(45) Date of Patent: Mar. 2, 2021

(54) MICROCELL SYSTEMS FOR DELIVERING ACTIVE MOLECULES

(71) Applicant: E Ink California, LLC, Fremont, CA (US)

(72) Inventor: Lei Liu, Fremont, CA (US)

(73) Assignee: E INK CALIFORNIA, LLC, Fremont, CA (US)

(*) Notice: Subject to any disclaimer, the term of this patent is extended or adjusted under 35 U.S.C. 154(b) by 0 days.

(21) Appl. No.: 16/733,385

(22) Filed: Jan. 3, 2020

(65) Prior Publication Data

US 2020/0138733 A1    May 7, 2020

Related U.S. Application Data

(62) Division of application No. 15/933,442, filed on Mar. 23, 2018, now abandoned.

(60) Provisional application No. 62/475,924, filed on Mar. 24, 2017.

(51) Int. Cl.
| | |
|---|---|
| *A61K 9/70* | (2006.01) |
| *A61K 9/00* | (2006.01) |
| *A61K 47/34* | (2017.01) |
| *A61K 47/32* | (2006.01) |
| *A61K 31/465* | (2006.01) |

(52) U.S. Cl.
CPC .......... *A61K 9/7092* (2013.01); *A61K 9/0021* (2013.01); *A61K 31/465* (2013.01); *A61K 47/32* (2013.01); *A61K 47/34* (2013.01)

(58) Field of Classification Search
CPC .... A61K 47/34; A61K 31/465; A61K 9/0021; A61K 47/32; A61K 9/7092
See application file for complete search history.

(56) References Cited

U.S. PATENT DOCUMENTS

| | | | |
|---|---|---|---|
| 4,559,222 A | 12/1985 | Enscore | |
| 4,640,689 A | 2/1987 | Sibalis | |
| 4,734,090 A | 3/1988 | Sibalis | |
| 5,125,894 A | 6/1992 | Phipps | |

(Continued)

FOREIGN PATENT DOCUMENTS

| | | |
|---|---|---|
| EP | 1457233 A1 | 9/2004 |
| KR | 19980025307 A | 7/1998 |
| WO | 2009073686 A1 | 6/2009 |

OTHER PUBLICATIONS

Harvey, T.G.; "Replication techniques for micro-optics"; SPIE Proc. vol. 3099, pp. 76-82; 1997. Jan. 1, 1997.

(Continued)

*Primary Examiner* — Jianfeng Song

(74) *Attorney, Agent, or Firm* — Ioannis Constantinides

(57) ABSTRACT

An active molecule delivery system whereby active molecules can be released on demand and/or a variety of different active molecules can be delivered from the same system and/or different concentrations of active molecules can be delivered from the same system. The active delivery system includes a plurality of microcells, wherein the microcells are filled with a medium including active molecules. The microcells include an opening, and the opening is spanned by a porous diffusion layer. The microcell arrays may be loaded with different active ingredients, thereby providing a mechanism to deliver different, or complimentary, active ingredients on demand.

19 Claims, 8 Drawing Sheets

(56) References Cited

U.S. PATENT DOCUMENTS

| | | |
|---|---|---|
| 5,135,479 A | 8/1992 | Sibalis |
| 5,486,362 A | 1/1996 | Kitchell |
| 5,533,995 A | 7/1996 | Corish |
| 5,591,767 A | 1/1997 | Mohr |
| 5,603,693 A | 2/1997 | Frenkel |
| 5,658,592 A | 8/1997 | Tanihara |
| 5,797,898 A | 8/1998 | Santini, Jr. |
| 5,931,804 A | 8/1999 | Sibalis |
| 5,980,943 A | 11/1999 | Ayer |
| 6,123,861 A | 9/2000 | Santini, Jr. et al. |
| 6,521,191 B1 | 2/2003 | Schenk |
| 6,564,093 B1 | 5/2003 | Ostrow |
| 6,757,560 B1 | 6/2004 | Fischer |
| 6,933,098 B2 | 8/2005 | Chan-Park |
| 6,980,855 B2 | 12/2005 | Cho |
| 7,229,556 B1 | 6/2007 | Hinds, III |
| 7,279,064 B2 | 10/2007 | Daniel |
| 7,315,758 B2 | 1/2008 | Kwiatkowski |
| 7,383,083 B2 | 6/2008 | Fischer |
| 7,392,080 B2 | 6/2008 | Eppstein et al. |
| 7,537,590 B2 | 5/2009 | Santini, Jr. |
| 7,604,628 B2 | 10/2009 | Santini, Jr. |
| 7,611,481 B2 | 11/2009 | Cleary |
| 7,715,088 B2 | 5/2010 | Liang |
| 7,892,221 B2 | 2/2011 | Santini, Jr. |
| 8,095,213 B1 | 1/2012 | Sexton |
| 8,257,324 B2 | 9/2012 | Prausnitz |
| 8,403,915 B2 | 3/2013 | Santini, Jr. |
| 8,440,222 B2 | 5/2013 | Hausner |
| 8,517,958 B2 | 8/2013 | Eppstein |
| 8,696,637 B2 | 4/2014 | Ross |
| 8,744,569 B2 | 6/2014 | Imran |
| 8,830,561 B2 | 9/2014 | Zang |
| 8,862,223 B2 | 10/2014 | Yanaki |
| 8,962,014 B2 | 2/2015 | Prinz |
| 8,968,699 B2 | 3/2015 | Jin |
| 9,186,317 B2 | 11/2015 | Smyth |
| 9,188,829 B2 | 11/2015 | Li |
| 9,320,720 B2 | 4/2016 | Maier |
| 9,326,979 B2 | 5/2016 | Kimura |
| 9,327,105 B2 | 5/2016 | Ramdas |
| 9,388,307 B2 | 7/2016 | Li |
| 9,610,440 B2 | 4/2017 | Jordan |
| 9,968,549 B2 | 5/2018 | Kosel |
| 10,087,344 B2 | 10/2018 | Moran |
| 2005/0191337 A1 | 9/2005 | Gueret |
| 2005/0228340 A1* | 10/2005 | Cleary .............. A61M 37/0015 604/46 |
| 2006/0009731 A1 | 1/2006 | Wu |
| 2006/0257450 A1 | 11/2006 | Mudumba |
| 2007/0196456 A1 | 8/2007 | Stevens |
| 2007/0248657 A1 | 10/2007 | Smith |
| 2007/0292463 A1 | 12/2007 | Spector |
| 2008/0020007 A1 | 1/2008 | Zang |
| 2009/0234214 A1 | 9/2009 | Santini, Jr. |
| 2010/0189793 A1 | 7/2010 | Meyer |
| 2011/0046557 A1 | 2/2011 | Lee |
| 2011/0111013 A1 | 5/2011 | Salman |
| 2011/0196474 A1 | 8/2011 | Davalian |
| 2012/0176663 A1* | 7/2012 | Zang .................... C09K 19/544 359/296 |
| 2013/0096486 A1 | 4/2013 | Schroeder |
| 2014/0330223 A1 | 11/2014 | Schurad |
| 2015/0301425 A1 | 10/2015 | Du |
| 2016/0045158 A1 | 2/2016 | Hsu |
| 2016/0279072 A1 | 9/2016 | Li |
| 2017/0205649 A1 | 7/2017 | Wang |
| 2018/0271800 A1 | 9/2018 | Liu |

OTHER PUBLICATIONS

Ebbert Jon O. et al., "Combination Pharmacotherapy for Stopping Smoking: What Advantages Does it Offer?", Drugs, vol. 70 No. 6, pp. 643-650, (Apr. 16, 2010). Apr. 16, 2010.

Kalyong Cal et al., "Magnetically triggered reversible Controlled Drug Delivery from Microfabricated Polymeric Multireservior Devices"., Advanced Materials. 2009, 21, 4045-4049 May 28, 2009.

Korean Intellectual Property Office, PCT/US2018/023917, International Search Report and Written Opinion, dated Jul. 10, 2017. Jul. 10, 2018.

Korean Intellectual Property Office, PCT/US2018/023928, International Search Report and Written Opinion, dated Jul. 10, 2018. Jul. 10, 2018.

Korean Intellectual Property Office, PCT/US2018/023921, International Search Report and Written Opinion, dated Jul. 10, 2018. Jul. 10, 2018.

Korean Intellectual Property Office, PCT/US2018/060259, International Search Report and Written Opinion, dated Apr. 29, 2019. Apr. 29, 2019.

Korean Intellectual Property Office, PCT/US2018/060266, International Search Report and Written Opinion, dated Apr. 29, 2019. Apr. 29, 2019.

Xuan, Shouhu et al., "Systhesis of Fe3O4@Polyaniline Core/Shell Microspheres with Well-Defined Blackberrym-Like Morphology", J. Phys. Chem. C., vol. 112, pp. 18804-9. (2008). Oct. 3, 2008.

Sahoo et al., "A Review of Transdermal drug delivery system", Journal der Pharmazie Forschung, vol. 2, N-1, 2013, 32-56 (2013) 2013.

Huang, W. C. et al.., "A flexible drug delivery chip for the magnetically-controlled release of anti-epileptic drugs", Journal of Controlled Release, vol. 139, Issue 3, Nov. 3, 2009, pp. 221-228 Nov. 3, 2009.

European Patent Office, EP Appl. No. 18771343.3, Extended European Search Report, dated Aug. 14, 2020. Aug. 14, 2020.

Gulati Gaurav Kumar et al., "Programmable carbon nanotube membrane-based transdermal nicotine delivery with microdialysis validation assay", Nanomedicine: Nanotechnology, Biology and medicine, Elsevier, NL, vol. 13, No. 1, Jul. 18, 2016, p. 1-9, XP029879755, ISSN: 1549-9634 (Jul. 18, 2016) Jul. 18, 2016.

Im J S et al., "The effect of carbon nanotubes on drug delivery in an electro-sensitive transdermal drug delivery system" Biomaterials, Elsevier, Amsterdam, NL, vol. 31, No. 6, Feb. 1, 2010, pp. 1414-1419, XP026814171, ISSN: 0142-9612 ( Feb. 1, 2010) Feb. 1, 2010.

European Patent Office, EP. Appl. No. 18772394.5, European Search Report, dated Nov. 30, 2020. Nov. 30, 2020.

European Patent Office, EP. Appl. No. 18771792.1, Supplemental Partial European Search Report, dated Nov. 24, 2020. Nov. 24, 2020.

* cited by examiner

MICROCELL SYSTEMS FOR DELIVERING ACTIVE MOLECULES

RELATED APPLICATIONS

This application claims benefit of application Ser. No. 15/933,442, filed on Mar. 23, 2018, where the Ser. No. 15/933,442 application is based on and claims priority to U.S. Provisional Application No. 62/475,924, filed Mar. 24, 2017. The entire contents of the aforementioned applications are incorporated herein by reference in their entirety.

BACKGROUND

Transdermal delivery of pharmaceutical agents has proven effective for drugs that are able to move across the skin barrier. For example, small amounts of nicotine can be delivered over extended periods with transdermal patches that suspend the nicotine in an ethylene vinyl acetate (EVA) copolymer. See, e.g., Nicoderm-CQ® by GlaxoSmithKline (Brentford, UK). Most of the commercially-available transdermal patches contain a matrix with only one drug, or a combination of drugs that are compatible for storage, such as oxycodone and tocopherol. See, e.g., TPM/Oxycodone patch from Phosphagenics, Ltd. (Melbourne, AU). Nonetheless, the efficacy of multi-component patches may degrade with time as the components interact. See, e.g., reports of crystallization in rotigotine transdermal patches (Nuepro®, UCB, Inc., Smyrna, Ga.).

Because there are a number of medications that are best administered in combination, there is a need for a simple (and inexpensive) delivery system that allows for the simultaneous delivery of multiple active components from the same transdermal system. Additionally, it would be beneficial if the delivery could be accomplished on demand sometime after the transdermal patch has been affixed to the skin.

SUMMARY

The invention addresses these needs by providing a transdermal delivery system whereby combinations of active molecules can be administered with the same device. Additionally, the systems of the invention allow for the delivery of different concentrations and/or different volumes of active molecules from the same delivery system.

Thus, in one aspect the invention is an active molecule delivery system including a plurality of microcells. The microcells may be square, round, or polygonal, such as a honeycomb structure. Each microcell includes an opening that is spanned by a porous diffusion layer. The porous diffusion layer may be constructed from a variety of materials, such acrylate, methacrylate, polycarbonate, polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene. Typically, each microcell has a volume greater than 100 nL, and the porous diffusion layer has an average pore size of between 1 nm and 100 nm.

In one embodiment, the system includes at least first and second microcells, wherein the first microcell includes a first active molecule and the second microcell includes a second active molecule, which is different from the first active molecule. In another embodiment, the system includes at least first and second microcells, wherein the first microcell includes a first concentration of an active molecule and the second microcell includes a second concentration of the active molecule, which is different from the first concentration. In another embodiment, the system includes at least first and second microcells, wherein the first microcell includes a first volume of a solution including an active molecule and the second microcell includes a second volume of the solution including the active molecule, wherein the two volumes are different. In another embodiment, the system includes at least first and second microcells, wherein the first microcell includes a first thickness in the portion of the porous diffusion layer over the opening of the first microcell and the second microcell includes a second thickness in the portion of the porous diffusion layer over the opening of the second microcell, wherein the two thicknesses are different. In another embodiment, the system includes at least first and second microcells, wherein the average pore size of the porous diffusion layer over the opening of the first microcell is different from the average pore size of the porous diffusion layer over the opening of the second microcell. In addition to varying the type and concentration of active molecules, it is also possible to prepare a system including an active and another useful compound such as a vitamin, adjuvant, etc. Other combinations of active molecules, agents, and concentrations will be evident to one of skill in the art.

In some embodiments, an active molecule is distributed in a biocompatible non-polar liquid, such as an oil, such as vegetable, fruit, or nut oil. In other embodiments, the active molecules are distributed in an aqueous liquid, such as water or an aqueous buffer. The mixtures may also include charge control agents, surfactants, nutrients, and adjuvants. Typically, the active molecule is a pharmaceutical compound, however systems of the invention can be used to deliver hormones, nutraceuticals, proteins, nucleic acids, antibodies, or vaccines.

In another aspect, a system is described including a plurality of microcells sealed with a sealing layer and a microneedle array including microneedles configured to penetrate through a microcell, thereby piercing the sealing layer and releasing an active molecule from the microcell. Such systems additionally include a compressible layer disposed between the microneedle array and the plurality of microcells. In some embodiments, the delivery system additionally includes an adhesive layer adjacent the sealing layer. The sealing layer may be, for example, methylcellulose, hydroxymethylcellulose, an acrylate, a methacrylate, a polycarbonate, a polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene. In some embodiments, the microneedles are at least 10 µm in length to provide sufficient length to traverse all the way though a microcell, for example at least 20 µm in length, at least 50 µm in length, at least 70 µm in length. Additionally, the microneedles may be hollow to provide passage of active molecules through the microneedles into a surface adjacent the delivery system. In some embodiments, the compressible layer includes a gas bladder, foam, or a hydrogel. In some embodiments the active molecule delivery system also includes an encapsulating backing to protect the system from physical disruption and to keep the delivery system secure against a surface.

BRIEF DESCRIPTION OF THE DRAWINGS

In FIGS. 5C and 5D a combination of top and bottom exposure is used, allowing the walls in one lateral direction to be cured by top photomask exposure, and the walls in another lateral direction to be cured bottom exposure through the opaque base conductor film;

FIG. 7A shows the system before the microneedles pierce the microcells and release the active molecules. FIG. 7B shows the system after the microneedles have been driven into and through the microcells, thereby releasing the active molecules into the surface below;

DETAILED DESCRIPTION

The invention provides an active molecule delivery system whereby active molecules can be released on demand and/or a variety of different active molecules can be delivered from the same system and/or different concentrations of active molecules can be delivered from the same system. The invention is well-suited for delivering pharmaceuticals to patients transdermally, however the invention may be used to deliver active ingredients, generally. For example, the invention can deliver tranquilizing agents to a horse during transport. The active delivery system includes a plurality of microcells, wherein the microcells are filled with a medium including active molecules. The microcells include an opening, and the opening is spanned by a porous diffusion layer. The microcell arrays may be loaded with different active ingredients, thereby providing a mechanism to deliver different, or complimentary, active ingredients on demand.

In addition to more conventional applications, such as transdermal delivery of pharmaceutical compounds, the active molecule delivery system may be the basis for delivering agricultural nutrients. For example, the microcell arrays can be fabricated into large sheets that can be used in conjunction with hydroponic growing systems, or the microcell arrays can be integrated into hydrogel film farming. See, for example, Mebiol, Inc. (Kanagawa, Japan). The active molecule delivery systems can also be incorporated into the structural walls of smart packing. Such delivery systems makes it possible to have long term release of antioxidants into a package containing fresh vegetables. This "smart" packaging will dramatically improve the shelf life of certain foods, and it will only require the amount of antioxidant necessary to maintain freshness until the package is opened. Thus, the same packaging can be used for food that is distributed locally, across the country, or around the globe.

The invention also provides a system for simple and low cost delivery of "cocktails" of active molecules on demand. Such a delivery system may be used, for example, as an emergency delivery system for a person undergoing an allergic reaction. The system may include epinephrine, as well as antihistamines. The device can be applied and then triggered to cause the actives to be quickly passed through the skin. The system may be particularly effective as a back-up system for small children who may be exposed to life-threatening allergens while on a field trip, etc. A parent can affix the delivery system to the child with instructions to activate the device in the event of, e.g., a bee sting. Because the device is relatively simple, compliance with proper delivery protocols will be greater than, e.g., an epipen.

Figure 1:
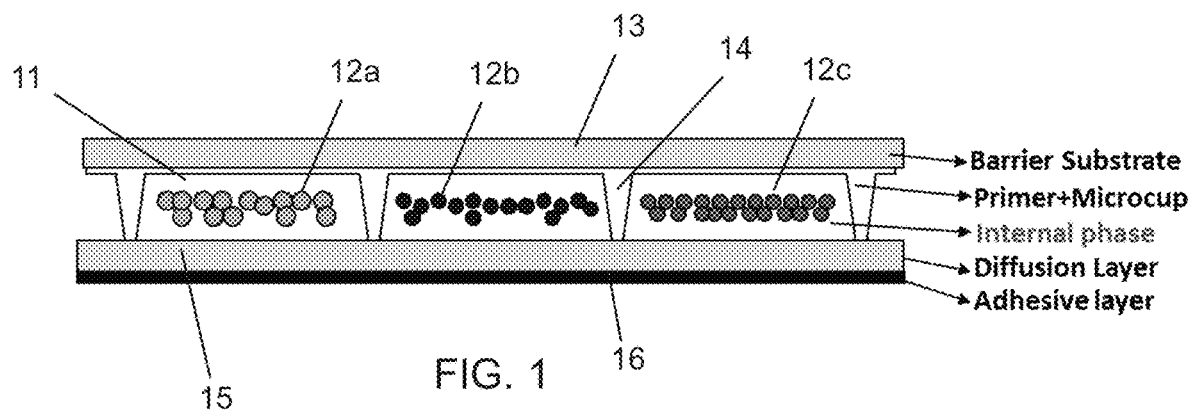
FIG. 1 illustrates an embodiment of an active molecule delivery system including a plurality of microcells including a porous diffusion layer wherein different active molecules are included in different microcells.

An overview of an active molecule delivery system is shown in FIG. 1. The system includes a plurality of microcells 11, each microcell including a medium (a.k.a. internal phase), that includes an active molecule 12a/b/c. As shown in FIG. 1, a first microcell may include a first active 12a, while a second microcell includes a second active 12b, while a third microcell includes a third active 12c. Each microcell 11 is part of an array that is formed from a polymer matrix, which is described in more detail below. The active molecule delivery system will typically include a backing barrier 13 to provide structural support and protection against moisture ingress and physical interactions. The microcells are defined by walls 14 that are at least 1 µm high, although they can be much higher depending upon the desired depth of the microcell. The microcells may be arranged as squares, a honeycomb, circles, etc. The microcell 11 will have an opening that is spanned by a porous diffusion layer 15, which may be constructed from a variety of natural or non-natural polymers, such as acrylates, methacrylates, polycarbonates, polyvinyl alcohols, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene. Often the system will additionally include an adhesive layer 16 that is also porous to the active molecule. The adhesive layer 16 assists in keeping the active molecule delivery system adjacent to the surface. Using picoliter injection with inkjet or other fluidic systems, individual microcells can be filled to enable a variety of different actives to be included in an active molecule delivery system.

Figure 2:
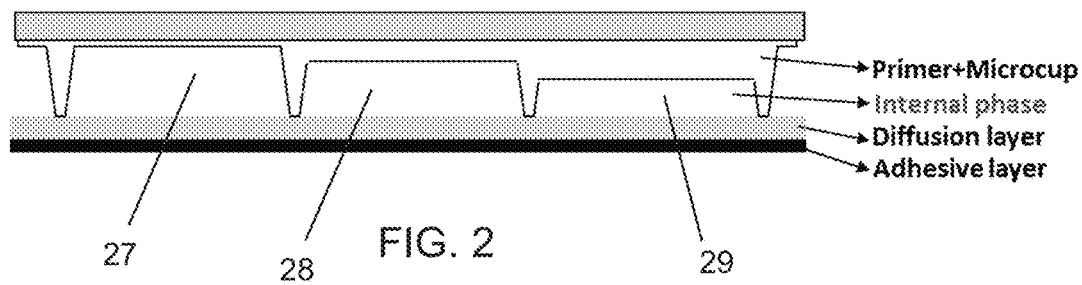
FIG. 2 illustrates an embodiment of an active molecule delivery system including a plurality of microcells including a porous diffusion layer wherein different microcells have different volumes.

FIG. 2 shows an alternative construction of an active molecule delivery system. In the construction of FIG. 2, the depth of different microcells 27, 28, 29 is varied by increasing the amount of polymer at the base of the microcell. This is easily accomplished by using a mold with the desired depth and the embossing technique described below. In other embodiments, the width of a microcell can be larger or smaller depending upon the volume of solution including an active that is desired to be contained within a given microcell.

Figure 3:
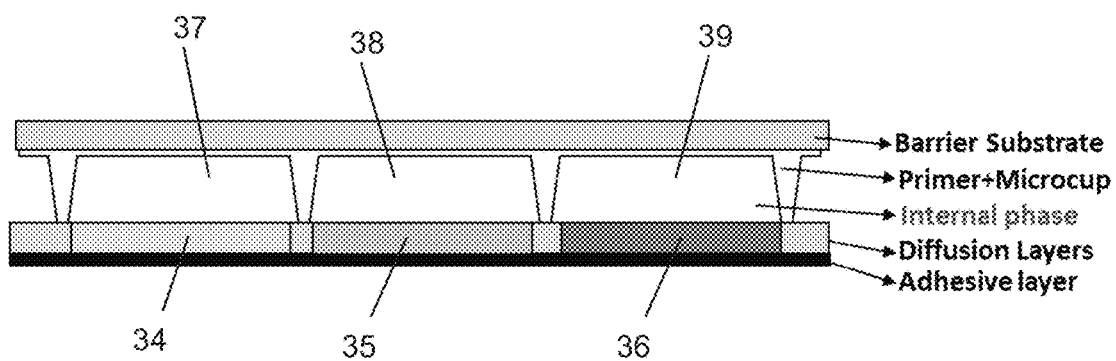
FIG. 3 illustrates an embodiment of an active molecule delivery system including a plurality of microcells including a porous diffusion layer wherein the opening to different microcells is spanned by porous diffusion layers having different average pore sizes.

FIG. 3 shows yet another embodiment of an active molecule delivery system in which the porosity of the diffusion layer is varied for different microcells. This can be accomplished by using different polymer materials and microinjection, e.g., using inkjet during the sealing process (described below). Such systems allow a single delivery system to administer varying concentrations of the same or different active molecules over a period of time. For example, a system of the invention may include three microcells 37, 38, 39 with nicotine at three different concentrations. However, the dosage time will be controlled by the porosity of the diffusion layer. For example, shortly after waking the most concentrated dose may be delivered via the first microcell 37 via the most porous diffusion layer 34, followed by a maintenance dose delivered from the second microcell 38, and then during the nighttime, the least concentrated dosage will be delivered via the third microcell 39 via the least porous diffusion layer 36.

Of course, a variety of combinations are possible, and varying microcells might include pharmaceuticals, nutraceuticals, adjuvants, vitamins, or vaccines. Furthermore, the arrangement of the microcells may not be distributed. Rather the microcells may be filled in clusters, which makes filling and sealing more straightforward. In other embodiments, smaller microcell arrays may be filled with the same medium, i.e., having the same active molecule at the same concentration, and then the smaller arrays assembled into a larger array to make a delivery system of the invention.

Techniques for Constructing Microcells.

Figure 4:
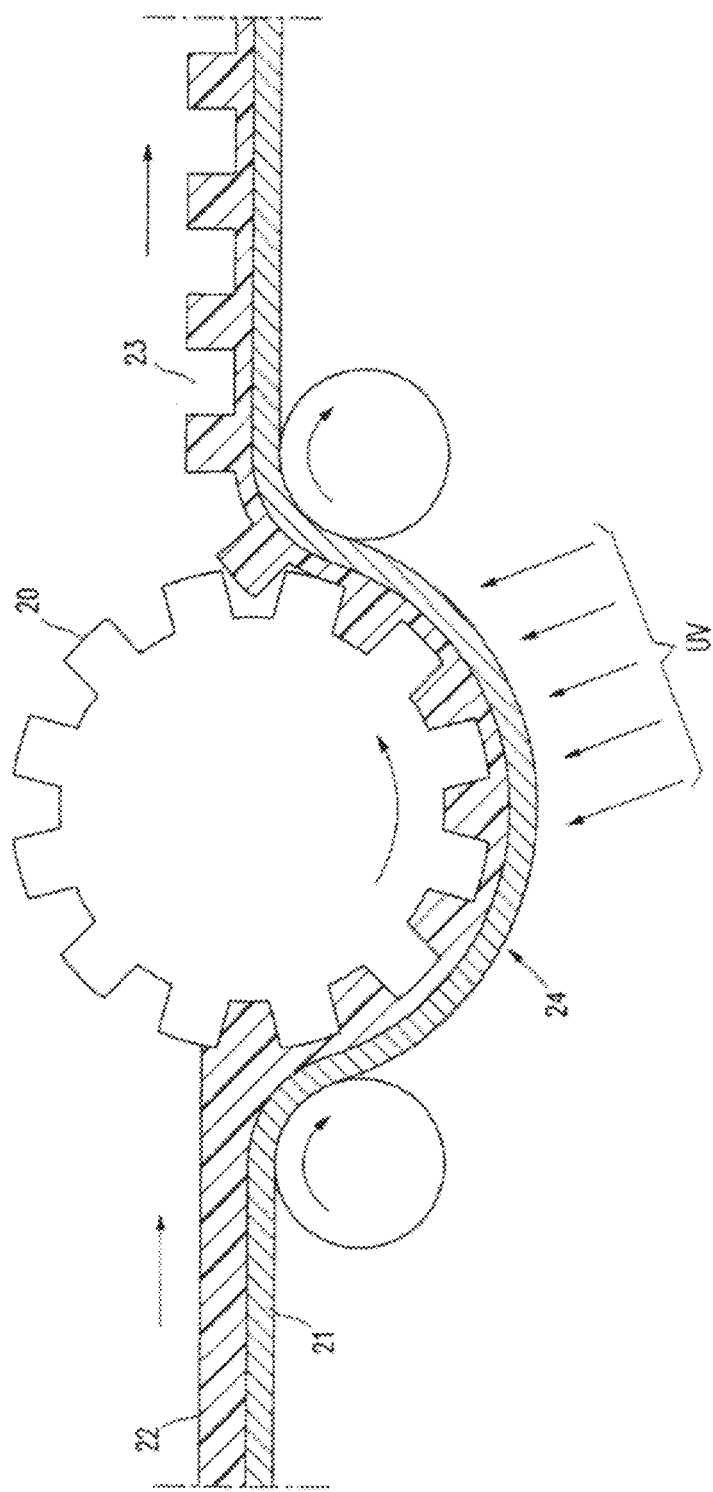
FIG. 4 shows a method for making microcells for the invention using a roll-to-roll process.

Microcells may be formed either in a batchwise process or in a continuous roll-to-roll process as disclosed in U.S. Pat. No. 6,933,098. The latter offers a continuous, low cost, high throughput manufacturing technology for production of compartments for use in a variety of applications including active molecule delivery and electrophoretic displays. Microcell arrays suitable for use with the invention can be created with microembossing, as illustrated in FIG. 4. A male mold 20 may be placed either above the web 24, as shown in FIG. 4, or below the web 24 (not shown) however alternative arrangements are possible. See U.S. Pat. No. 7,715,088, which is incorporated herein by reference in its entirety. A conductive substrate may be constructed by forming a conductor film 21 on polymer substrate that becomes the backing for a device. A composition comprising a thermoplastic, thermoset, or a precursor thereof 22 is then coated on the conductor film. The thermoplastic or thermoset precursor layer is embossed at a temperature higher than the glass transition temperature of the thermoplastics or thermoset precursor layer by the male mold in the form of a roller, plate or belt.

The thermoplastic or thermoset precursor for the preparation of the microcells may be multifunctional acrylate or methacrylate, vinyl ether, epoxide and oligomers or polymers thereof, and the like. A combination of multifunctional epoxide and multifunctional acrylate is also very useful to achieve desirable physico-mechanical properties. A cross-linkable oligomer imparting flexibility, such as urethane acrylate or polyester acrylate, may be added to improve the flexure resistance of the embossed microcells. The composition may contain polymer, oligomer, monomer and additives or only oligomer, monomer and additives. The glass transition temperatures (or $T_g$) for this class of materials usually range from about 70° C. to about 150° C., preferably from about 20° C. to about 50° C. The microembossing process is typically carried out at a temperature higher than the $T_g$. A heated male mold or a heated housing substrate against which the mold presses may be used to control the microembossing temperature and pressure.

As shown in FIG. 4, the mold is released during or after the precursor layer is hardened to reveal an array of microcells 23. The hardening of the precursor layer may be accomplished by cooling, solvent evaporation, cross-linking by radiation, heat or moisture. If the curing of the thermoset precursor is accomplished by UV radiation, UV may radiate onto the transparent conductor film from the bottom or the top of the web as shown in the two figures. Alternatively, UV lamps may be placed inside the mold. In this case, the mold must be transparent to allow the UV light to radiate through the pre-patterned male mold on to the thermoset precursor layer. A male mold may be prepared by any appropriate method, such as a diamond turn process or a photoresist process followed by either etching or electroplating. A master template for the male mold may be manufactured by any appropriate method, such as electroplating. With electroplating, a glass base is sputtered with a thin layer (typically 3000 Å) of a seed metal such as chrome inconel. The mold is then coated with a layer of photoresist and exposed to UV. A mask is placed between the UV and the layer of photoresist. The exposed areas of the photoresist become hardened. The unexposed areas are then removed by washing them with an appropriate solvent. The remaining hardened photoresist is dried and sputtered again with a thin layer of seed metal. The master is then ready for electroforming. A typical material used for electroforming is nickel cobalt. Alternatively, the master can be made of nickel by electroforming or electroless nickel deposition. The floor of the mold is typically between about 50 to 400 microns. The master can also be made using other microengineering techniques including e-beam writing, dry etching, chemical etching, laser writing or laser interference as described in "Replication techniques for micro-optics", SPIE Proc. Vol. 3099, pp. 76-82 (1997). Alternatively, the mold can be made by photomachining using plastics, ceramics or metals.

Prior to applying a UV curable resin composition, the mold may be treated with a mold release to aid in the demolding process. The UV curable resin may be degassed prior to dispensing and may optionally contain a solvent. The solvent, if present, readily evaporates. The UV curable resin is dispensed by any appropriate means such as, coating, dipping, pouring or the like, over the male mold. The dispenser may be moving or stationary. A conductor film is overlaid the UV curable resin. Pressure may be applied, if necessary, to ensure proper bonding between the resin and the plastic and to control the thickness of the floor of the microcells. The pressure may be applied using a laminating roller, vacuum molding, press device or any other like means. If the male mold is metallic and opaque, the plastic substrate is typically transparent to the actinic radiation used to cure the resin. Conversely, the male mold can be transparent and the plastic substrate can be opaque to the actinic radiation. To obtain good transfer of the molded features onto the transfer sheet, the conductor film needs to have good adhesion to the UV curable resin which should have a good release property against the mold surface.

Photolithography.

Figure 5A:
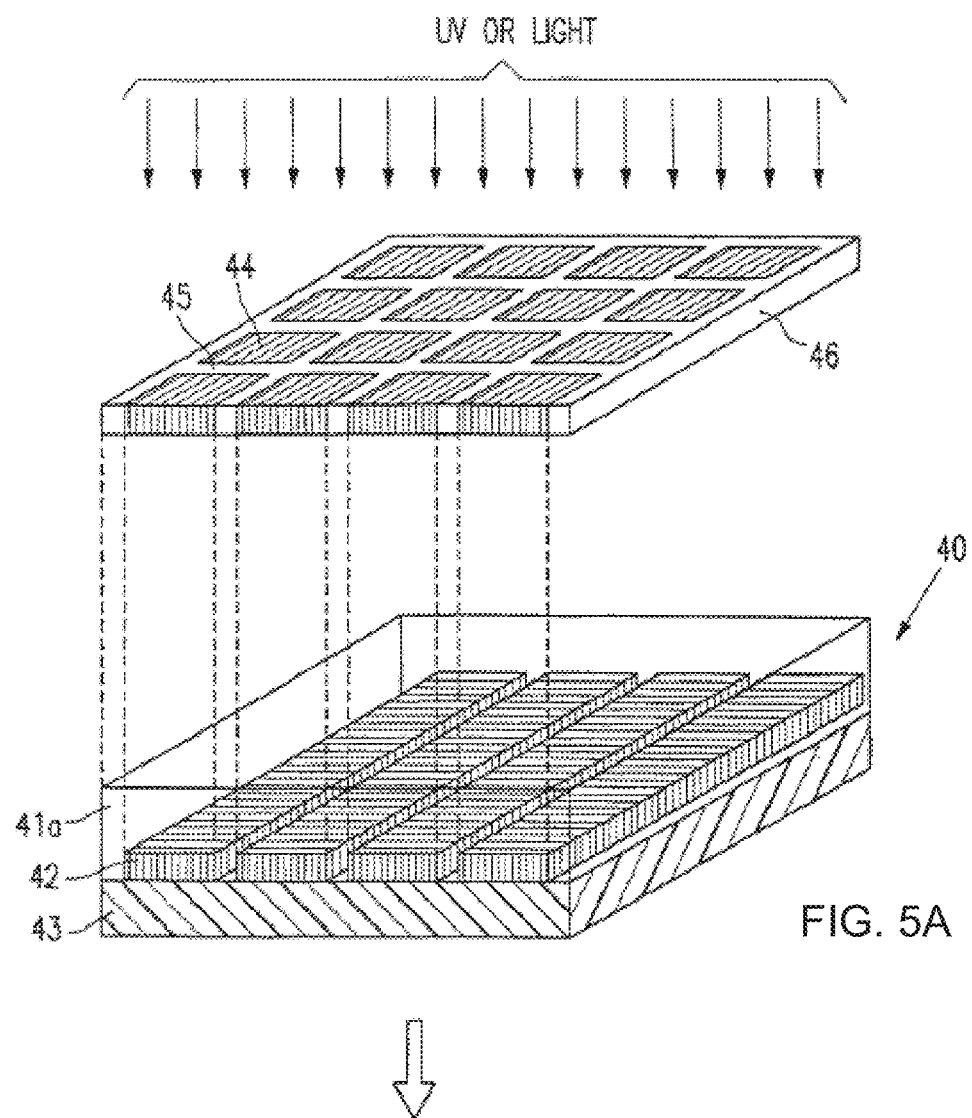
FIGS. 5A and 5B detail the production of microcells for an active molecule delivery system using photolithographic exposure through a photomask of a conductor film coated with a thermoset precursor.
Figure 5B:
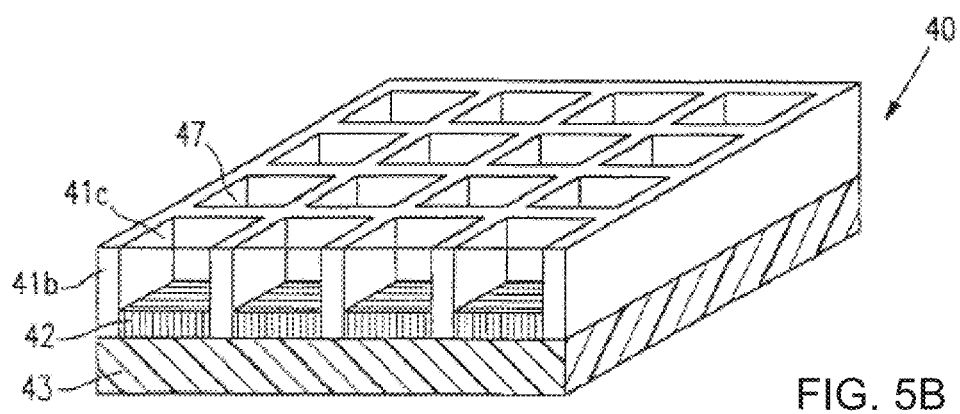

Microcells can also be produced using photolithography. Photolithographic processes for fabricating a microcell array are illustrated in FIGS. 5A and 5B. As shown in FIGS. 5A and 5B, the microcell array 40 may be prepared by exposure of a radiation curable material 41a coated by known methods onto a conductor electrode film 42 to UV light (or alternatively other forms of radiation, electron beams and the like) through a mask 46 to form walls 41b corresponding to the image projected through the mask 46. The base conductor film 42 is preferably mounted on a supportive substrate base web 43, which may comprise a plastic material.

In the photomask 46 in FIG. 5A, the dark squares 44 represent the opaque area and the space between the dark squares represents the transparent area 45 of the mask 46. The UV radiates through the transparent area 45 onto the radiation curable material 41a. The exposure is preferably performed directly onto the radiation curable material 41a, i.e., the UV does not pass through the substrate 43 or base conductor 42 (top exposure). For this reason, neither the substrate 43, nor the conductor 42, needs to be transparent to the UV or other radiation wavelengths employed.

As shown in FIG. 5B, the exposed areas 41b become hardened and the unexposed areas (protected by the opaque area 44 of the mask 46) are then removed by an appropriate solvent or developer to form the microcells 47. The solvent or developer is selected from those commonly used for dissolving or reducing the viscosity of radiation curable materials such as methylethylketone (MEK), toluene, acetone, isopropanol or the like. The preparation of the microcells may be similarly accomplished by placing a photomask underneath the conductor film/substrate support web and in this case the UV light radiates through the photomask from the bottom and the substrate needs to be transparent to radiation.

Imagewise Exposure.

Figure 5D:
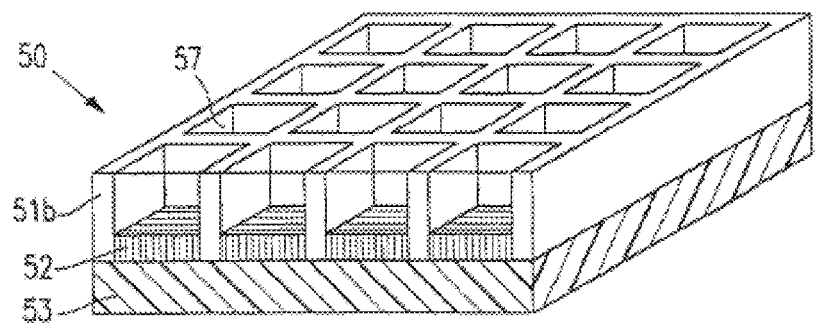
FIGS. 5C and 5D detail an alternate embodiment in which microcells for an active molecule delivery system are fabricated using photolithography.
Figure 5C:
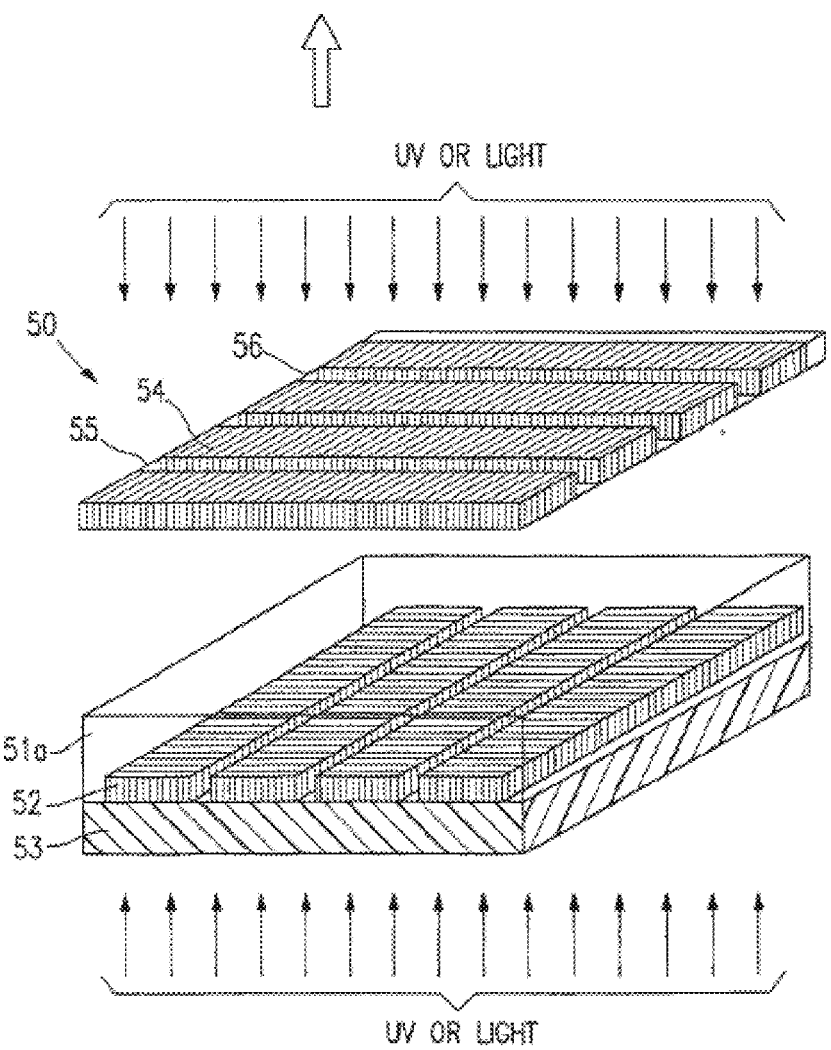

Still another alternative method for the preparation of the microcell array of the invention by imagewise exposure is illustrated in FIGS. 5C and 5D. When opaque conductor lines are used, the conductor lines can be used as the photomask for the exposure from the bottom. Durable microcell walls are formed by additional exposure from the top through a second photomask having opaque lines perpendicular to the conductor lines. FIG. 5C illustrates the use of both the top and bottom exposure principles to produce the microcell array 50 of the invention. The base conductor film 52 is opaque and line-patterned. The radiation curable material 51a, which is coated on the base conductor 52 and substrate 53, is exposed from the bottom through the conductor line pattern 52 which serves as the first photomask. A second exposure is performed from the "top" side through the second photomask 56 having a line pattern perpendicular to the conductor lines 52. The spaces 55 between the lines 54 are substantially transparent to the UV light. In this process, the wall material 51b is cured from the bottom up in one lateral orientation, and cured from the top down in the perpendicular direction, joining to form an integral microcell 57. As shown in FIG. 5D, the unexposed area is then removed by a solvent or developer as described above to reveal the microcells 57. The technique described in FIGS. 5C and 5D thus allow the different walls to be constructed with different porosity, as needed for the embodiment illustrated in FIG. 3.

The microcells may be constructed from thermoplastic elastomers, which have good compatibility with the microcells and do not interact with the electrophoretic media. Examples of useful thermoplastic elastomers include ABA, and (AB)n type of di-block, tri-block, and multi-block copolymers wherein A is styrene, α-methylstyrene, ethylene, propylene or norbonene; B is butadiene, isoprene, ethylene, propylene, butylene, dimethylsiloxane or propylene sulfide; and A and B cannot be the same in the formula. The number, n, is ≥1, preferably 1-10. Particularly useful are di-block or tri-block copolymers of styrene or ox-methylstyrene such as SB (poly(styrene-b-butadiene)), SBS (poly(styrene-b-butadiene-b-styrene)). SIS (poly(styrene-b-styrene)), SEBS (poly(styrene-b-ethylene/butylenes-b-stylene)) poly(styrene-b-dimethylsiloxane-b-styrene), poly (α-methylstyrene-b-isoprene), poly(α-methylstyrene-b-isoprene-b-α-methylstyrene), poly(α-methylstyrene-b-propylene sulfide-b-α-methylstyrene), poly(α-methylstyrene-b-dimethylsiloxane-b-α-methylstyrene).

Commercially available styrene block copolymers such as Kraton D and G series (from Kraton Polymer, Houston, Tex.) are particularly useful. Crystalline rubbers such as poly(ethylene-co-propylene-co-5-methylene-2-norbomene) or EPDM (ethylene-propylene-diene terpolymer) rubbers such as Vistalon 6505 (from Exxon Mobil, Houston, Tex.) and their grafted copolymers have also been found very useful.

The thermoplastic elastomers may be dissolved in a solvent or solvent mixture which is immiscible with the display fluid in the microcells and exhibits a specific gravity less than that of the display fluid. Low surface tension solvents are preferred for the overcoating composition because of their better wetting properties over the microcell walls and the electrophoretic fluid. Solvents or solvent mixtures having a surface tension lower than 35 dyne/cm are preferred. A surface tension of lower than 30 dyne/cm is more preferred. Suitable solvents include alkanes (preferably $C_{6-12}$ alkanes such as heptane, octane or Isopar solvents from Exxon Chemical Company, nonane, decane and their isomers), cycloalkanes (preferably $C_{6-12}$ cycloalkanes such as cyclohexane and decalin and the like), alkylbezenes (preferably mono- or di-$C_{1-6}$ alkyl benzenes such as toluene, xylene and the like), alkyl esters (preferably $C_{2-5}$ alkyl esters such as ethyl acetate, isobutyl acetate and the like) and $C_{3-5}$ alkyl alcohols (such as isopropanol and the like and their isomers). Mixtures of alkylbenzene and alkane are particularly useful.

In addition to polymer additives, the polymer mixtures may also include wetting agents (surfactants). Wetting agents (such as the FC surfactants from 3M Company, Zonyl fluorosurfactants from DuPont, fluoroacrylates, fluoromethacrylates, fluoro-substituted long chain alcohols, perfluoro-substituted long chain carboxylic acids and their derivatives, and Silwet silicone surfactants from OSi, Greenwich, Conn.) may also be included in the composition to improve the adhesion of the sealant to the microcells and provide a more flexible coating process. Other ingredients including cross-linking agents (e.g., bisazides such as 4,4'-diazidodiphenyl-methane and 2,6-di(4'-azidobenzal)-4-methylcyclohexanone), vulcanizers (e.g., 2-benzothiazolyl disulfide and tetramethylthiuram disulfide), multifunctional monomers or oligomers (e.g., hexanediol, diacrylates, trimethylolpropane, triacrylate, divinylbenzene, diallylphthalene), thermal initiators (e.g., dilauroryl peroxide, benzoyl peroxide) and photoinitiators (e.g., isopropyl thioxanthone (ITX), Irgacure 651 and Irgacure 369 from Ciba-Geigy) are also highly useful to enhance the physico-mechanical properties of the sealing layer by crosslinking or polymerization reactions during or after the overcoating process.

After the microcells are produced, they are filled with appropriate mixtures of active molecules. The microcell array 60 may be prepared by any of the methods described above. As shown in cross-section in FIGS. 6A-6D, the microcell walls 61 extend upward from the substrate 63 to form the open cells. The microcells may include a primer layer 62 to passivate the mixture and keep the microcell material from interacting with the mixture containing the actives 65. Prior to filling, the microcell array 60 may be cleaned and sterilized to assure that the active molecules are not compromised prior to use.

Figure 6A:
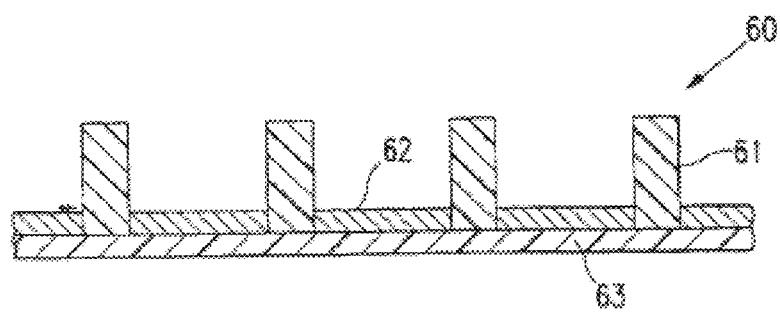
FIGS. 6A-6D illustrate the steps of filling and sealing an array of microcells to be used in an active molecule delivery system.
Figure 6B:
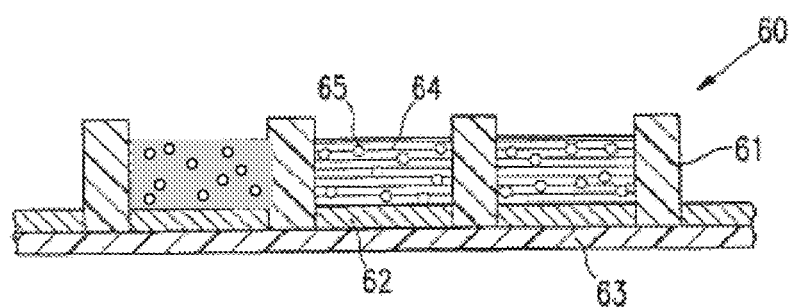

The microcells are next filled with a mixture 64 including active molecules 65. As shown in FIG. 6B, different microcells may include different actives. The microcells 60 are preferably partially filled to prevent overflow and the unintentional mixing of active ingredients. In systems for delivering hydrophobic active molecules, the mixture may be based upon a biocompatible oil or some other biocompatible hydrophobic carrier. For example, the mixture may comprise a vegetable, fruit, or nut oil. In other embodiments, silicone oils may be used. In systems for delivering hydrophilic active molecules, the mixture may be based upon water or another aqueous medium such as phosphate buffer. The mixture need not be a liquid, however, as hydrogels and other matrices may be suitable to deliver the active molecules 65.

The microcells may be filled using a variety of techniques. In some embodiments, where a large number of neighboring microcells are to be filled with an identical mixture, blade coating may be used to fill the microcells to the depth of the microcell walls 61. In other embodiments, where a variety of different mixtures are to filled in a variety of nearby microcell, inkjet-type microinjection can be used to fill the microcells. In yet other embodiments, microneedle arrays may be used to fill an array of microcells with the correct mixtures. The filling may be done in a one-step, or a multistep process. For example, all of the cells may be partially filled with an amount of solvent. The partially filled microcells are then filled with a second mixture including the one or more active molecules to be delivered.

Figure 6C:
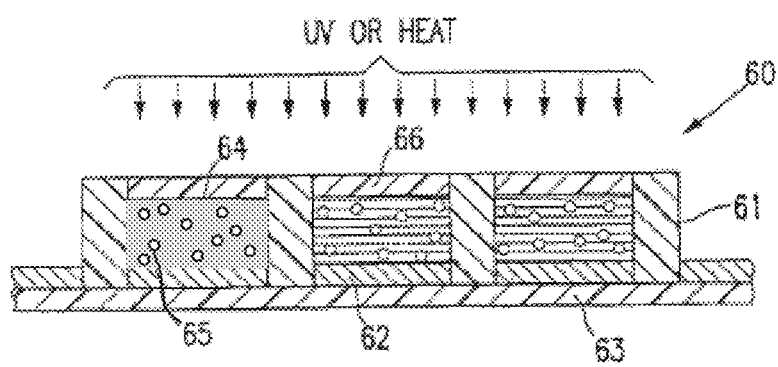
Figure 6D:
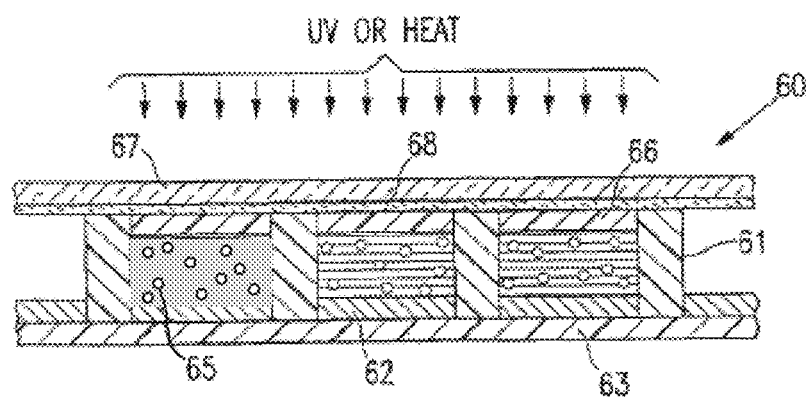

As shown in FIG. 6C, after filling, the microcells are sealed by applying a polymer 66 that becomes the porous diffusion layer. In some embodiments, the sealing process may involve exposure to heat, dry hot air, or UV radiation. In most embodiments the polymer 66 will be compatible with the mixture 64, but not dissolved by the solvent of the mixture 64. The polymer 66 will also be biocompatible and selected to adhere to the sides or tops of the microcell walls 61. A suitable biocompatible adhesive for the porous diffusion layer is a phenethylamine mixture, such as described in U.S. patent application Ser. No. 15/336,841, filed Oct. 30, 2016 and titled "Method for Sealing Microcell Containers with Phenethylamine Mixtures," which is incorporated herein by reference in its entirety. Accordingly, the final microcell structure is mostly impervious to leaks and able to withstand flexing without delamination of the porous diffusion layer.

In alternate embodiments, a variety of individual microcells may be filled with the desired mixture by using iterative photolithography. The process typically includes coating an array of empty microcells with a layer of positively working photoresist, selectively opening a certain number of the microcells by imagewise exposing the positive photoresist, followed by developing the photoresist, filling the opened microcells with the desired mixture, and sealing the filled microcells by a sealing process. These steps may be repeated to create sealed microcells filled with other mixtures. This procedure allows for the formation of large sheets of microcells having the desired ratio of mixtures or concentrations.

After the microcells 60 are filled, the sealed array may be laminated with a finishing layer 68 that is also porous to the active molecules, preferably by pre-coating the finishing layer 68 with an adhesive layer which may be a pressure sensitive adhesive, a hot melt adhesive, or a heat, moisture, or radiation curable adhesive. The laminate adhesive may be post-cured by radiation such as UV through the top conductor film if the latter is transparent to the radiation. In some embodiments, a biocompatible adhesive 67 is then laminated to the assembly. The biocompatible adhesive 67 will allow active molecules to pass through while keeping the device mobile on a user. Suitable biocompatible adhesives are available from 3M (Minneapolis, Minn.).

Figure 7A:
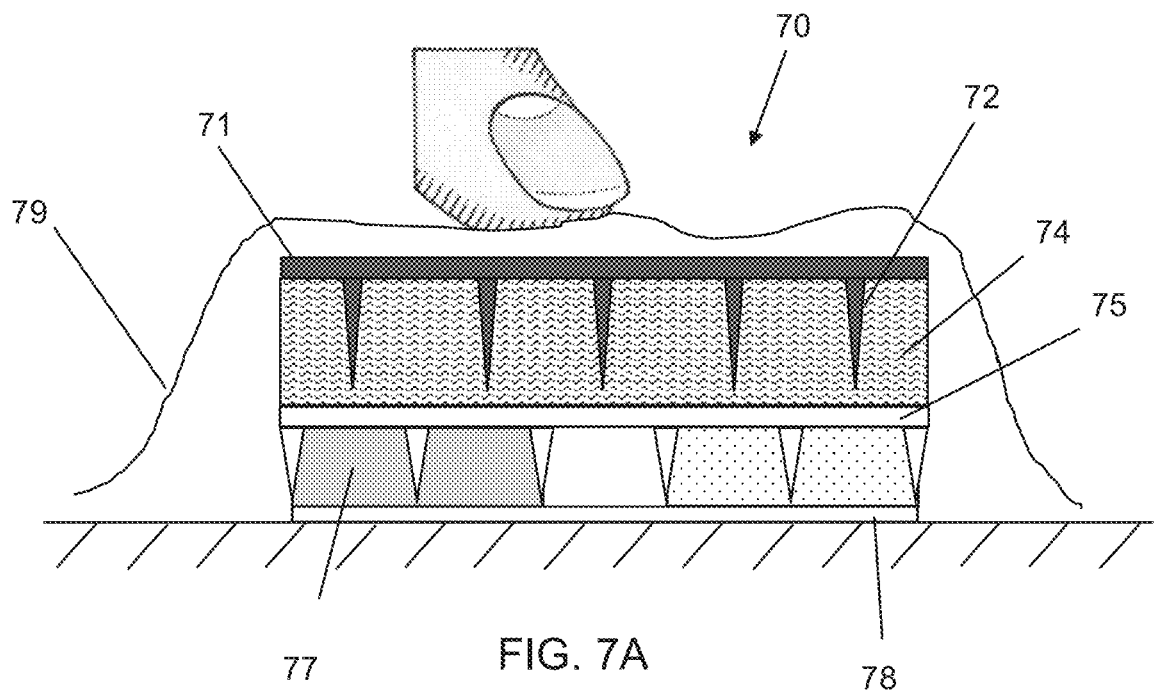
FIGS. 7A and 7B illustrate the use of a system for delivering active molecules that includes microcells, a compressible layer, and an array of microneedles. The scale of the microcells, compressible layer, and microneedles is exaggerated for clarity.
Figure 7B:
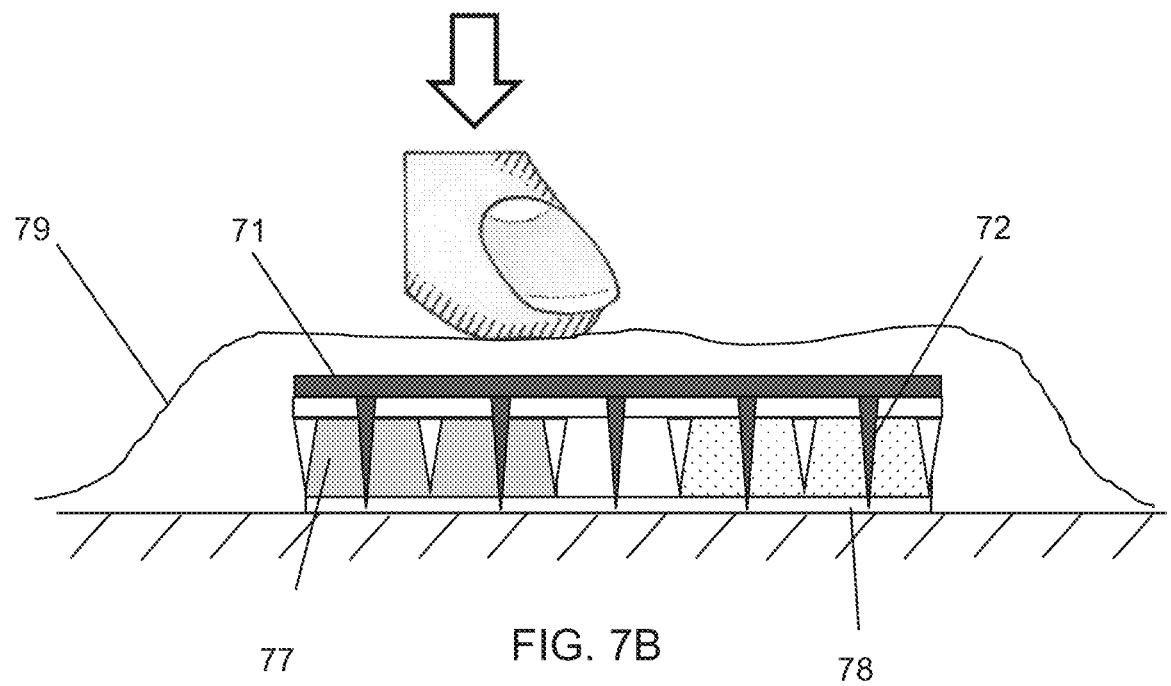

Once the deliver system has been constructed, it may be covered with an encapsulating backing 79 to provide protection against physical shock. Such an encapsulating backing 79 is shown in FIGS. 7A-7B however the thickness of the encapsulating backing 79 has been exaggerated for clarity. The encapsulating backing may also include adhesives to make sure that the active molecule delivery system stays affixed, e.g., to a patient's back. The encapsulating backing 79 may also include aesthetic coloring or fun designs for children.

Microneedle Array/Microcell Array Systems.

In other aspects, it is beneficial to provide an inexpensive active molecule delivery system that is shelf-stable and provides on-demand delivery of the active molecules. An active molecule delivery system 70 including a microneedle array 71 is shown in FIGS. 7A and 7B. The microneedle array 71 includes a plurality of microneedles 72 that are designed to puncture the substrate 75 of the microcells in the assembly, move through the microcell 77, and finally to pierce a sealing layer 78 that retains the mixture containing the active molecule within the microcell 77. The microneedles can be formed from polymers, metal, or semiconductors, and the microneedles can be formed with contact printing, grown with epitaxy, built up with photolithography, or deposited with ion beam deposition. The microneedles can be solid or hollow. The microneedles can be formed with openings that allow the active molecules to pass from the side of the microneedles into the lumen of the needle and out the tip into the surface to which the delivery device is attached.

Between the microneedle array 71 and the substrate of the microcells 75 is disposed a compressible material 74 that is designed to deform and allow the microneedle assembly 71 to travel to and into the microcells (compare FIGS. 7A and 7B). The compressible material 74 may be a gel or a foam. The gel or foam may include a polymer material, such as polyethylene. Alternatively, the compressible material 74 may be a gas-filled bladder that simply deforms or folds as pressure is put against the back of the microcell assembly by a user. The microneedle array 71, the compressible material 74, and the microcells are covered by an encapsulating backing 79, which may be formed from an elastomeric material to allow it to flex as the active molecule delivery system is compressed and the microneedles 72 are driven through the microcells.

The sealing layer 78 may be porous in some applications, however, it will be more common for the sealing layer 78 to form a barrier that prevents any fluid contained within the microcell 77 from escaping until the sealing layer 78 is pierced by the microneedle 72. The sealing layer 78 may be constructed from any of the materials listed above with respect to the porous diffusion layer. In addition, the sealing layer 78 can also be constructed from poly(vinylpyrrolidone) and hydroxymethylcellulose. As depicted in FIGS. 7A and 7B, the microcells 77 contain mixtures with different active molecules, however, different microcells may contain different concentrations of the same active molecules, or other combinations as discussed above. In fact, any of the active delivery systems described above may be coupled with a microneedle array to allow on-demand activation of the active delivery system.

EXAMPLE

Nicotine Release from Microcell Delivery System

Figure 8:
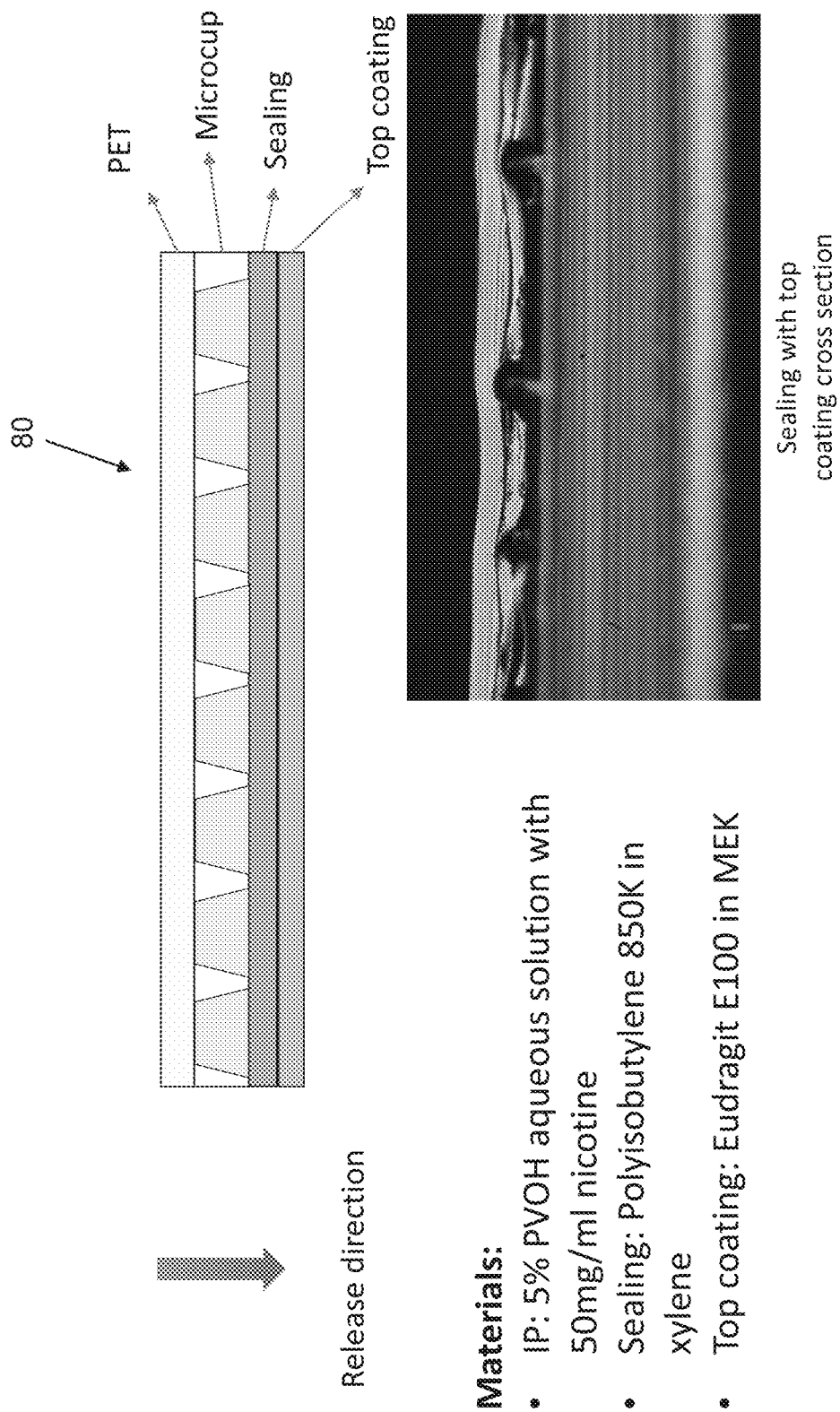
FIG. 8 shows a prototypical microcell delivery system and a microscope image of the porous diffusion layer that includes a layer of polyisobutylene and a layer of an acrylic/methacrylic acid copolymer (EUDRAGIT®, Evonik, Essen, Del.)

An active molecule delivery system including microcells and a porous diffusion layer was developed to evaluate delivery of an aqueous solution of nicotine. FIG. 8 shows the design of the delivery system used for the test. The system 80 includes a plurality of microcells formed with embossing as described above with respect to FIG. 4. The microcells were filled with an aqueous 50 mg/ml solution of nicotine that included 5% of polyvinyl alcohol. The filled microcells were then sealed with a two-part porous diffusion layer that was deposited in two separate coatings. The first layer (a.k.a. sealing layer) is formed from polyisobutylene in xylene where the polyisobutylene has an average molecular weight of 850 kD. Once the polyisobutylene has cured, a final top coating is applied by spreading a methyl ethyl ketone solution of copolymers derived from esters of acrylic and methacrylic acid (Eudragit E100; EVONIC). The resulting two-part diffusion layer was examined under a microscope to determine that the polyisobutylene about 10 µm thick and the acrylic/methacrylic acid layer was about 15 µm. (See microscope image shown in FIG. 8)

Figure 9:
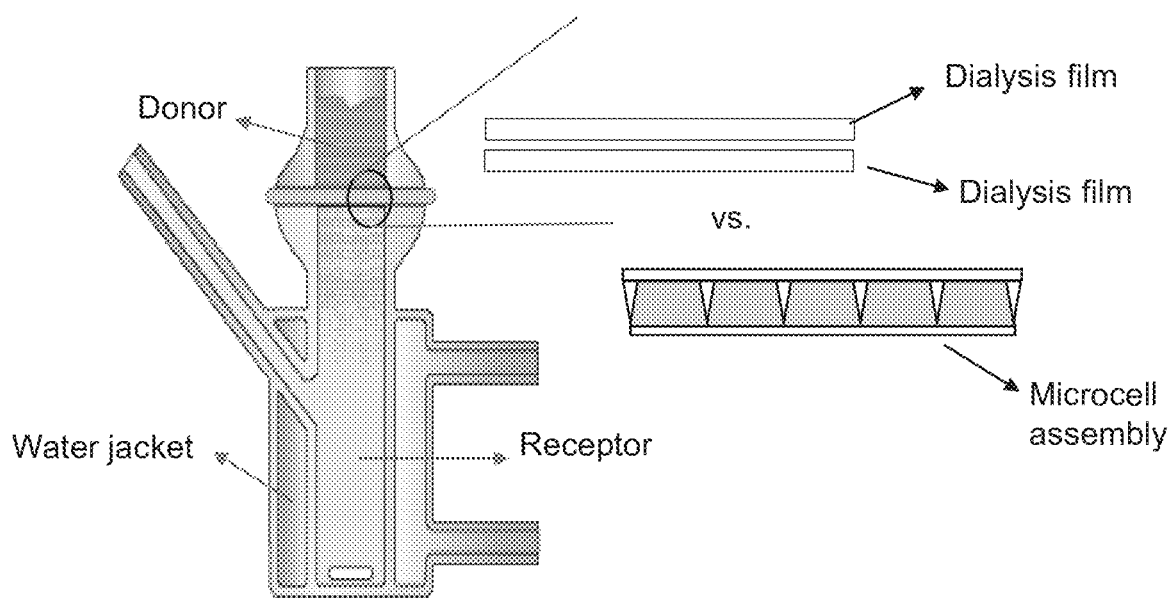
FIG. 9 illustrates the use of a Franz cell for measuring rates of diffusion through a double layer of dialysis film (control) and a microcell assembly of the invention.

The delivery rate of the microcell delivery system of FIG. 8 was evaluated using a Franz cell. The experimental setup is illustrated in FIG. 9. In brief, a Pyrex Franz cell (PermeGear, Inc., Hellertown, Pa.) was assembled as shown. As a control, two layers of dialysis tubing (Thermo-Fisher, Waltham, Mass.) were cut to fit across the opening at the joint of the Franz cell. 500 µL of a 1.3 mg/mL solution of nicotine in D.I. water was pipetted into the top of the cell. This provided a total load of approximately 0.7 mg of nicotine on the donor side of the Franz cell. The receptor cell was filled with 5 mL of D.I. water. After the nicotine solution was introduced to the donor cell, samples were removed from the receptor cell at various time points as indicated in the graph in FIG. 10. The samples were later analyzed to determine the total amount of nicotine that had passed through the double layer barrier, thereby resulting in the data points represented by the squares in FIG. 10.

The microcell delivery system described above (filled with 50 mg/ml of nicotine) was evaluated by removing the double layer of dialysis tubing, cleaning the Franz cell, and placing the microcell assembly at the neck joint. The total area of the microcell assembly was about 0.8 cm², resulting in a total volume of about 1.4 µL of the 50 mg/ml solution of nicotine, or a total load of approximately 0.07 mg of nicotine. As before, the receptor cell was filled with 5 mL of D.I. water, and samples were removed from the receptor cell at various time points as indicated in the graph in FIG. 10. The resulting data is represented by the circles in FIG. 10.

Figure 10:
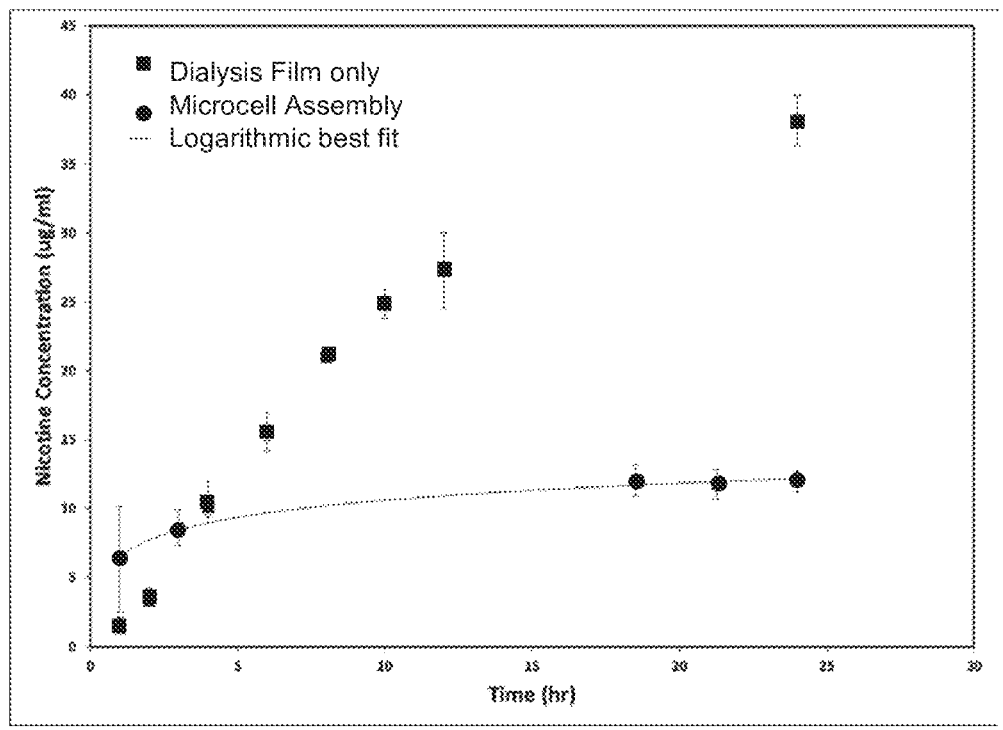
FIG. 10 shows nicotine release profiles through a double layer of dialysis film (control) and a microcell assembly of the invention.

As can be seen in FIG. 10, the microcell assembly released its nicotine much faster and more efficiently than the dialysis tubing (control). Regarding FIG. 10, it is clear that for the microcell delivery system, the receptor cell achieved a steady state concentration of nicotine in a few hours or less, while the control had not leveled out after more than 24 hours. Furthermore, despite having approximately one-tenth the amount of drug loading, the microcell assembly delivered almost a third of the total nicotine delivered by the control. That is, the microcell assembly achieved approximately 90% efficiency in delivering nicotine into the receptor cell while the control only achieved about 30% efficiency after 24 hours. The speed and efficacy of the microcell delivery system suggests that it may be very effective for administering alkaloid pain medications with water solubility similar to nicotine, such as morphine and oxycodone.

Thus the invention provides for an active molecule delivery system including a plurality of microcells. The microcells may include differing active molecules, or differing concentrations of active molecules. The microcells include an opening that is spanned by a porous diffusion layer. Microcell delivery systems may be supplemented with microneedle arrays that provide a low-cost way to have on-demand delivery of active molecules. This disclosure is not limiting, and other modifications to the invention, not described, but self-evident to one of skill in the art, are to be included in the scope of the invention.

The invention claimed is:

1. An active molecule delivery system comprising:
    a plurality of microcells, each microcell including a floor and walls creating an opening, having a total thickness between 25 and 50 µm, containing a mixture comprising an active molecule, and the opening of each microcell being sealed with a sealing layer having a thickness between 0.5 µm and 8 µm;
    a microneedle array comprising a plurality of microneedles at least 50 µm in length, wherein the plurality of microneedles is formed from polymers, metal, semiconductors or combinations thereof; and
    a compressible layer disposed between the microneedle array and the plurality of microcells, wherein the microneedles are configured to penetrate through a microcell, thereby piercing the sealing layer and releasing the active molecule from the microcell.

2. The active molecule delivery system of claim 1, wherein the plurality of microneedles is formed with contact printing, grown with epitaxy, built up with photolithography, or deposited with ion beam deposition.

3. The active molecule delivery system of claim 1, wherein the plurality of microneedles are solid.

4. The active molecule delivery system of claim 1, wherein the plurality of microneedles are hollow.

5. The active molecule delivery system of claim 1, wherein the plurality of microneedles comprise openings.

6. The active molecule delivery system of claim 5, wherein the openings allow the active molecules to pass from the side of the microneedles into the lumen of the needles and out the tip into the surface to which the delivery system is attached.

7. The active molecule delivery system of claim 1, wherein the compressible layer comprises a compressible material comprising a gel or a foam.

8. The active molecule delivery system of claim 7, wherein the gel or foam comprises a polymer.

9. The active molecule delivery system of claim 8, wherein polymer is polyethylene.

10. The active molecule delivery system of claim 1, wherein the compressible layer comprises a compressible material comprising a gas-filled bladder.

11. The active molecule delivery system of claim 10, wherein the gas-filled bladder deforms or folds as pressure is applied against the back of the microcell assembly.

12. The active molecule delivery system of claim 1, wherein the compressible layer and the plurality of microcells are covered by an encapsulating backing.

13. The active molecule delivery system of claim 12, wherein the encapsulating backing comprises an elastomeric material.

14. The active molecule delivery system of claim 1, wherein the sealing layer is porous.

15. The active molecule delivery system of claim 1, wherein the sealing layer is nonporous.

16. The active molecule delivery system of claim 1, wherein the sealing layer comprises an acrylate, a methacrylate, a polycarbonate, a polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, polystyrene, polyvinylpyrrolidone, hydroxymethylcellulose, or mixtures thereof.

17. The active molecule delivery system of claim 1, wherein the plurality of microcells, includes first and second microcells, wherein the first microcell includes a first active molecule, and the second microcell includes a second active molecule different from the first active molecule.

18. The active molecule delivery system of claim 1, wherein the active molecule is distributed in a biocompatible non-polar liquid or in an aqueous liquid.

19. The active molecule delivery system of claim 1, wherein the microcell is formed from multifunctional acrylates or methacrylates.

* * * * *